United States Patent [19]
Ohlson

[11] Patent Number: 5,023,899
[45] Date of Patent: Jun. 11, 1991

[54] METHOD AND ARRANGEMENT FOR X-RAY PHOTOGRAPHY OR THE LIKE

[76] Inventor: Carl-Eric Ohlson, Vintervagen 25, S-171 34 Solna, Sweden

[21] Appl. No.: 435,467
[22] PCT Filed: Jun. 18, 1987
[86] PCT No.: PCT/SE87/00288
  § 371 Date: Dec. 5, 1989
  § 102(e) Date: Dec. 5, 1989
[87] PCT Pub. No.: WO88/10095
  PCT Pub. Date: Dec. 29, 1988
[51] Int. Cl.$^5$ .............................................. H05G 1/02
[52] U.S. Cl. .................................... 378/196; 378/177; 378/181; 378/197; 378/91
[58] Field of Search ............... 378/167, 190, 197, 196, 378/91, 189, 181, 177

[56] References Cited

U.S. PATENT DOCUMENTS

| | | | |
|---|---|---|---|
| 4,024,401 | 5/1977 | Bernstein et al. | 378/197 |
| 4,358,856 | 11/1982 | Stivender et al. | 378/167 |
| 4,365,342 | 12/1982 | Vepy | 378/173 |
| 4,365,344 | 12/1982 | Dornheim | 378/189 |
| 4,365,345 | 12/1982 | Craig et al. | 378/190 |
| 4,412,346 | 10/1983 | Takenouti et al. | 378/190 |
| 4,417,356 | 11/1983 | Hoffman | 378/181 |
| 4,761,805 | 8/1988 | Sebring | 378/167 |

Primary Examiner—Edward P. Westin
Assistant Examiner—Kim-Kwok Chu
Attorney, Agent, or Firm—Fleit, Jacobson, Cohn, Price, Holman & Stern

[57] ABSTRACT

For taking X-ray photographs there is provided a moveable tower structure for ceiling-mounted frame which carries a beam source arranged for movement in X-Y-Z directions and which is rotatable about a horizontal axis. A receptor unit is mounted beneath a patient support table for movement in the X direction and Y direction. Activation of a holder associated with the receptor unit and intended to receive a vertically extending secondary receptor for horizontal beam path causes the beam source to move automatically to a basic setting.

15 Claims, 10 Drawing Sheets

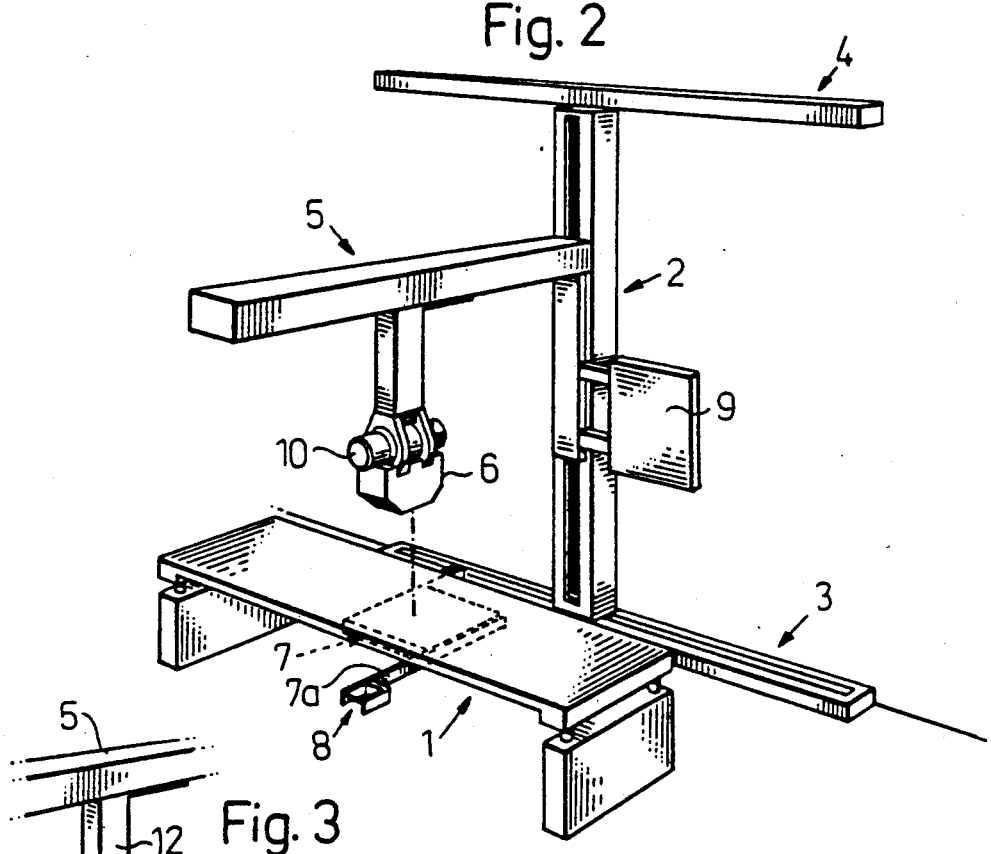
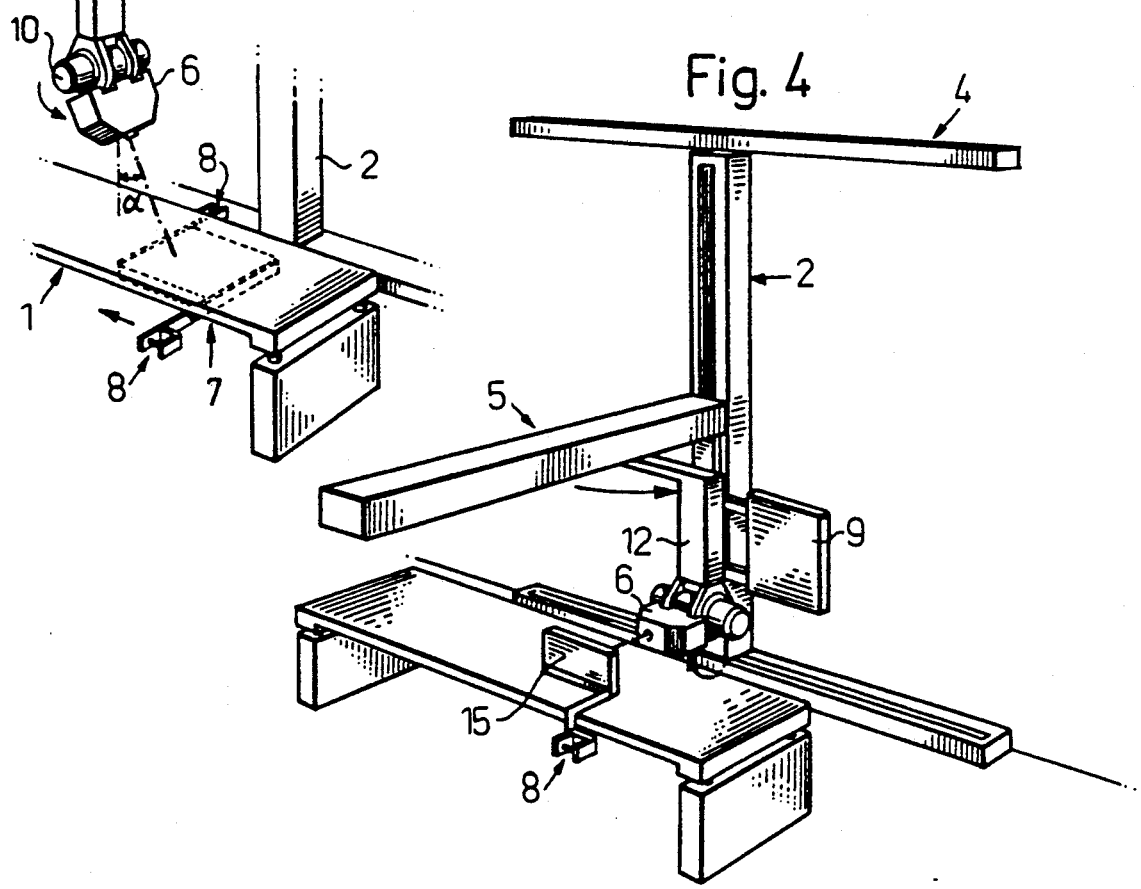

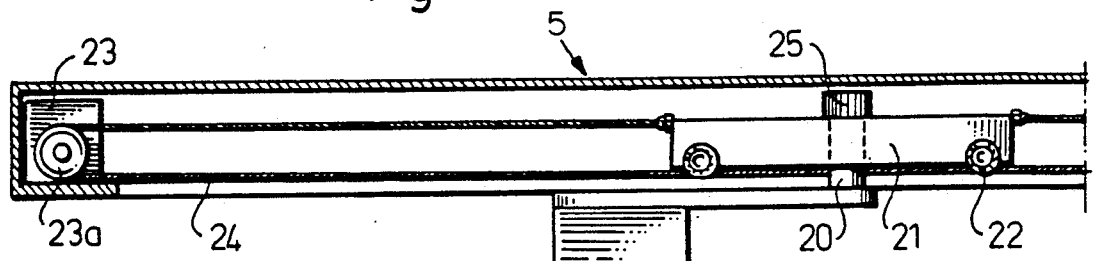
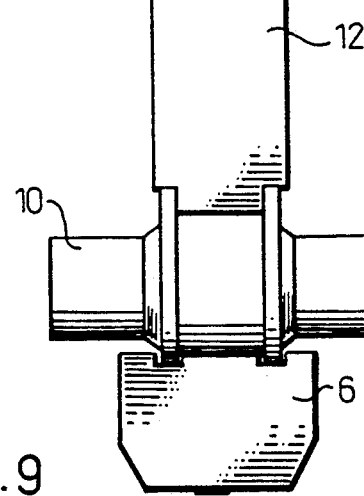
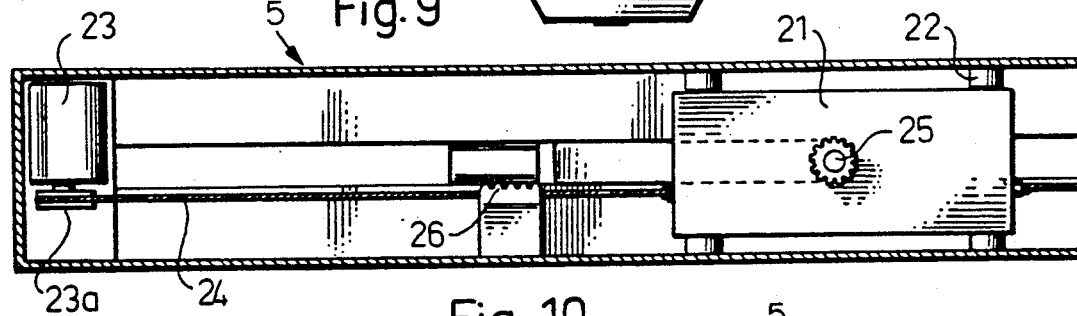
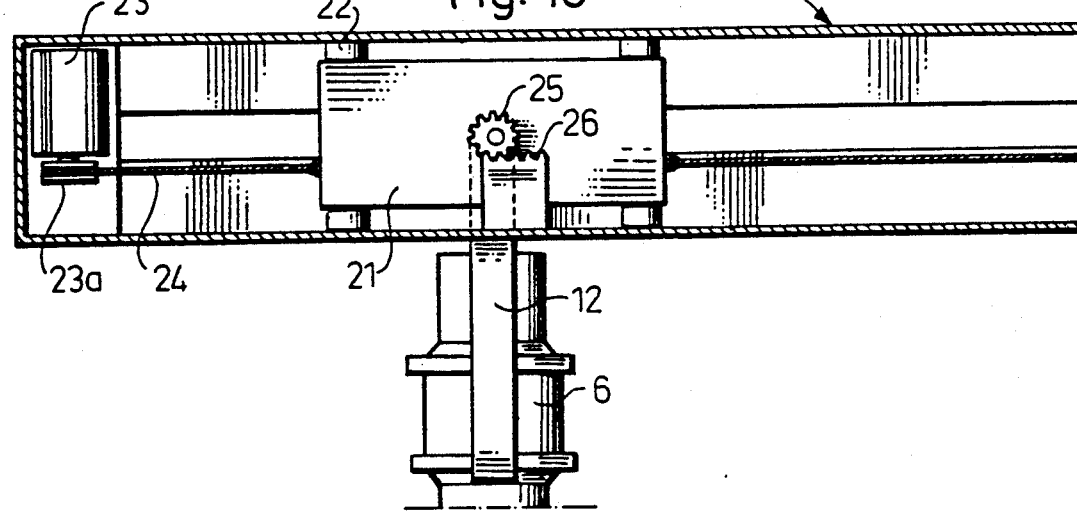

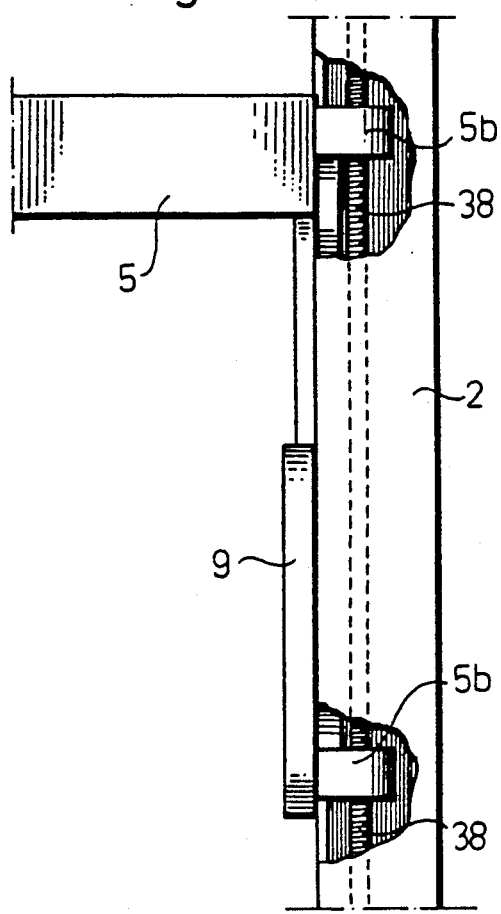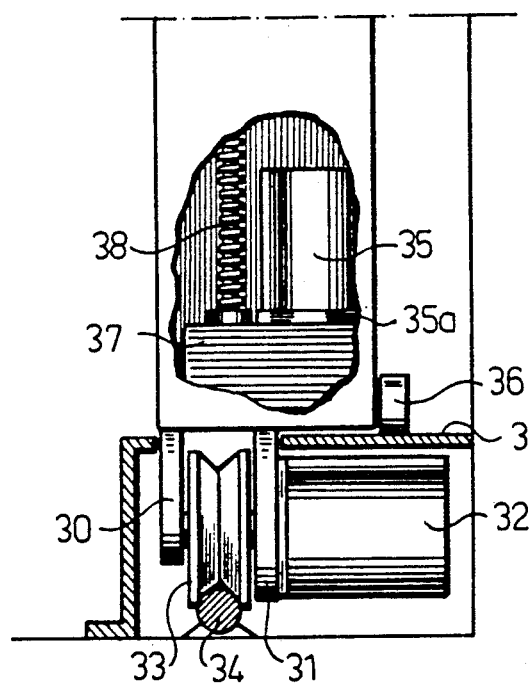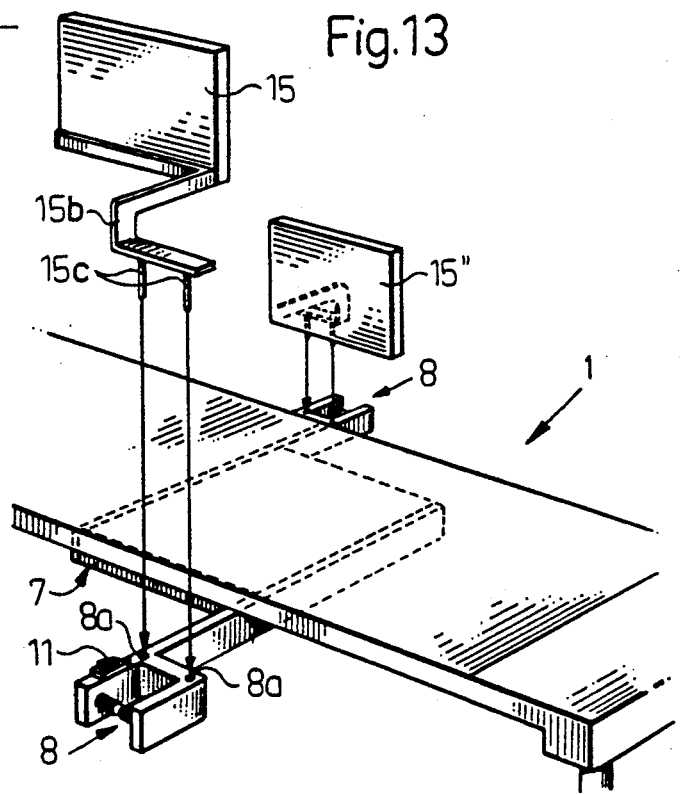

METHOD AND ARRANGEMENT FOR X-RAY PHOTOGRAPHY OR THE LIKE

TECHNICAL FIELD

The present invention relates to a method for taking X-ray photographs or the like with the aid of a beam source which is carried for movement in X, Y and Z directions and which is rotatable about a horizontal axis, and also with the aid of a patient support table and a receptor unit which is positioned beneath the table and capable of being moved in the X and Y directions and which when displaced automatically instigates movement of the beam source.

By X-direction is meant here and in the following a direction of movement parallel with one long side of the patient support table, and by Y-direction is meant a direction of movement perpendicular to the extension of said one long side, i.e. movement parallel to the short side of the table. The patient support table may therewith be adjusted to mutually different positions in relation, for instance, to a tower column or ceiling-support tower which carries the beam source. In all instances the expression "X-direction" refers to movement parallel with the long side of the table.

The invention also relates to X-ray photography apparatus.

BACKGROUND PRIOR ART

U.S. Pat. No. 4,365,345 (Craig et al) describes apparatus of this kind, in which, however, the beam source is located beneath the table in the actual patient investigation part of the apparatus, and the image receptor is located on a tower structure arranged above said patient investigation part. When the beam source is moved in the X- and Y-directions these movements are transferred to the receptor over a servo system. In this case, the actual patient investigation part is expansive and space consuming and is found difficult to work with by the X-ray personnel. Another significant drawback with this known apparatus is that there is no possibility of taking side photographs with a horizontally directed beam path.

U.S. Pat. No. 4,024,403 (Bernstein et al) teaches a conventional tower structure with manual adjustment of the patient support table, an overlying beam source and a receptor located beneath the table. The apparatus includes an electrical auxiliary device for adjusting the beam source angle and synchronized movement of the receptor corresponding to said angular adjustment, such that the central beam will always impinge on the patient at the correct angle.

The work required from the X-ray personnel with this type of X-ray equipment is both laborious and complicated, placing great strain on the shoulders and back muscles of the personnel as a result of the manual adjustment movements which must be carried out, not least the displacement of the heavy beam source. This equipment also lacks a facility for taking side photographs with horizontal beam path.

U.S. Pat. No. 4,365,344 (Dornheim) provides an example of apparatus incorporating mechanical synchronization between the setting movements of the receptor and beam source. This arrangement utilizes a complicated lever system, which makes the work carried out by the X-ray personnel both heavy and complicated, primarily because of the large masses which need to be activated, and also because of the stretching and bending required of said personnel. Furthermore, the receptor part of the apparatus must be lifted up each time a side photograph is taken. The possibility of taking angled photographs is limited.

U.S. Pat. No. 3,492,482 (Forsyth) describes and illustrates a beam source which is mounted on a vertical tower structure and which is movable in the Z-direction, and a receptor part which is moved synchronously with the beam source on a corresponding vertical tower structure. The apparatus is intended exclusively for taking side photographs with horizontal beam path, and the apparatus consequently has a limited field of use.

GB-B-1,323,769 (Picket Corp) describes apparatus comprising a receptor part in a patient support table and an overlying ceiling-carried beam source. This apparatus affords the possibility of taking side photographs with horizontal beam path, by swinging-up the patient support table about a horizontal axis and pivoting the beam source. The apparatus also enables the image size and shutter setting to be varied in relation to the beam-source/receptor distance ("SID", i.e. "source-image-distance"). Movement of the beam source and swinging of the patient support table, however, must be effected manually, circumstances which are also experienced as troublesome by the X-ray personnel.

SE-B-7906060-5 (Philips) describes a similar arrangement of apparatus, although in this case the beam source is located in the pivotal patient support table and the image receptor is located on a ceiling-carried frame structure, even though it is stated in the descriptive part of the specification that the arrangement may be reversed. Movements of the receptor and beam source in the X-direction are synchronized. When swinging up the table incorporating the beam source, the receptor is rotated around the horizontal axis synchronously therewith. It is also stated that the receptor and beam source can also moved synchronously in the Y-direction, although this is not illustrated in the specification.

This arrangement of apparatus also has the drawbacks associated with a pivotal patient support table, inter alia because of the large masses which need to be set in motion when taking side photographs, and because of the limited use possibilities of the apparatus in general. For example, there is no facility for taking side photographs of a seated patient. In summary it can be said that all apparatus or equipment of this kind lack the requisite flexibility.

Other examples of known X-ray tower structures are described and illustrated in DE-A1-3,406,717 (Philips), DE-A1-2,831,058 (Philips) and U.S. Pat. No. 4,501,011 (Hauck et al).

THE OBJECTS OF THE INVENTION

One object of the present invention is to provide an X-ray photography method which will avoid the aforesaid drawbacks, and other drawbacks, associated with known methods and which will enable X-ray photographs to be taken with vertical, horizontal and angled beam path with the aid of solely a single beam source without discomfort to the patient, i.e. without needing to manipulate the patient or the patient support table to any appreciable extend when adjusting the positions of the various X-ray devices, and without requiring heavy and laborious adjustment work to be carried out by the X-ray personnel. Neither shall the patient himself/herself need to cooperate actively in the investigation.

A further object is to provide a method of the aforesaid kind which will facilitate the work of the operator, particularly in those cases where different types of photographs are to be taken.

Still a further object of the invention is to provide a method of the aforesaid kind which offers increased flexibility, with the aid of simple means, i.e. so that the X-ray equipment enables photographs to be taken other than the "normal" photographs of a lying patient with vertical, horizontal or angled beam path, such as photographs of a sitting or standing patient for example.

A particular object of the invention is to provide a method and a system of apparatus which will enable a large number of mutually varying types of photographs to be taken without imposing difficulties on the X-ray personnel or discomfort to the patient, or in other words a universal system of apparatus for use in conjunction with X-ray photography.

SUMMARY OF THE INVENTION

These and other objects are fulfilled by a method according to the invention, which is mainly characterized in that activation of a receptor unit associated with a secondary receptor extending in the vertical plane results in, optionally after a time delay, automatic movement of the beam source to a basic setting for horizontal, centered beam path onto the secondary receptor.

Correspondingly, activation of the primary receptor located beneath the patient support table, optionally after a time delay, causes the beam source to return to a basic setting for vertical beam path from the primary receptor.

It is preferred in practice that the beam source in each basic setting position is caused to take a pre-determined distance from respective receptors.

The invention affords the important advantage that X-ray personnel need only manipulate the small mass exhibited by the receptor unit, which is located at a comfortable working height beneath the patient support table, whereafter all setting movements of the heavy beam source are effected through the agency of separate, servo-controlled drive units.

In certain cases the secondary receptor may be stationarily mounted on the movable receptor unit. One requirement in this regard, however, is that the secondary receptor will not cause an obstruction when the patient is transferred to the table or when adjustments are to be made to the position of the primary receptor.

Preferably, however, the secondary image receptor is mounted on a holder associated with and movable together with the primary unit, prior to activating the receptor.

To this end, the receptor unit may include, for instance, several types of holder means into which the secondary receptor can be placed. Alternatively, the secondary receptor may be connected to the receptor unit by a pivotal holder means which will enable the secondary receptor to be dropped to a "parking position" when not in use. In this case, the receptor is applied by being swung-up to its active position, prior to activation of the secondary receptor.

When moving the beam source to either of its basic setting positions, the source is swung through 90° around the horizontal axis and also moves in the Z-direction. Normally, movement also takes place in the X- and/or Y-directions. The beam source auxiliary means receives information relating to the type of secondary receptor used and the subsequent activating operation will result in pre-determined movement of the relevant beam source drive means.

Normally, it is desirable to place the receptor as close as possible to the patient, in order to obtain optimum image sharpness. In certain types of known X-ray equipment particular difficulties are experienced in taking side photographs with horizontal beam path, since this equipment has not been sufficiently prepared for such photographs. Consequently, in the case of some patients it is necessary to make provisional arrangement for holding the receptor, and in certain instances it may be necessary for the patient himself to hold the receptor.

Unsuitable arrangements such as these can be avoided when practicing the present invention, since the invention provides mutually different secondary receptors, from which the most suitable receptor for the purpose in question can be selected in each particular case. The apparatus is also able to detect the type of receptor used in each particular case, therewith enabling adjustments and/or collimation of the beam source to be carried out automatically when necessary.

It also lies within the scope of the invention to provide the possibility of using a secondary receptor carried on telescopic arms, so that the receptor can be brought into the close proximity of the patient. In this case the beam source will obtain information relating to the prevailing setting position of the receptor so that the beam source is adjusted automatically to a position corresponding to the receptor setting.

When photographing such parts of the body as the spine, kidneys and other organs with the patient in a recumbent position, the object will normally be located close to the table top. In this case, with selection of a suitable film or receptor format, the receptor should be located close to the table top in order for the object to lie in the center. In order to maintain a constant SID, the necessary adjustment movements are facilitated while ensuring, at the same time, optimum image quality.

For example, a secondary receptor holder can be placed on each side of the receptor unit, i.e. on each side of the patient support table. In the manner aforedescribed, the apparatus detects the location of the secondary receptor and the position of the beam force is adjusted accordingly.

Furthermore, the invention has the important advantage of affording the greatest possible protection to the patient, which is, of course, of particular benefit when taking X-ray photographs of unconscious and/or seriously injured patients. When practicing the present invention, such patients need not be moved, irrespective of the type of X-ray photographs to be taken.

Another important advantage afforded by the invention is that the pattern of movement carried out by the beam source can be programmed so that none of the movable components or parts need be brought to a position which is so close to the table as to cause injury to the patient. Expressed in another way, it can be said that the movement pattern of the equipment components shall be programmed in a manner such as to create a protective shell around a patient on the patient support table.

Particular advantages are also afforded when photographing with an angled beam path. In this case, the receptor unit will preferably exhibit a grid comprising mutually parallel lamellae which extend in the X-direction. The setting of the beam source is automatically adjusted in dependence on the angle of inclination to which said beam source is set, so that the beam path will always be centered relative to the receptor.

This will greatly reduce, or even eliminate, the risk of taking blurred or completely erroneous photographs, and also the risk of subjecting the patient unnecessarily to an excessively high dosage of X-ray because of the need to re-take photographs.

In this regard, it is possible, within the concept of the invention, for the apparatus to indicate the type of grid used, e.g. with the aid of a visual display or some other manner, which in turn will correct SID automatically in relation to the collimated beam source. At the same time, it is possible to make desired and suitable changes to the focus distance, with the purpose of achieving desired yields of the exposures made. As a complement to the table receptor, with its possibility of using one or more secondary receptors, it also lies within the concept of the invention to provide a tertiary receptor, for instance on a tower structure forming part of the equipment apparatus, or a separate tower structure, which may be a static fixture or movable. The most important purpose of a tower-carried receptor is that of enabling lung photographs to be taken, in which case the patient normally stands facing towards and close to the receptor. In this case, it is suitable for the receptor holder to face laterally outwards from the tower structure.

A third basic setting position relating to a tertiary receptor can also be utilized for taking other normally occurring photographs, e.g. a loaded knee, hip etc. In this case, the tertiary receptor is lowered to a suitable height, the beam source automatically following the movement carried out by said receptor.

The patient support table may be made longer than is normally the case, so as to provide at one end of the table a space in which a seat can be placed so as to enable photographs to be taken with the patient in a sitting position, e.g. sinus investigations, which are often carried out in conjunction with a lung X-ray. The seat unit is preferably capable of moving in the longitudinal direction of the table and is also preferably rotatable. The primary receptor unit located beneath the patient table can also be used even when the seat unit is being used. In this case, a further, specially designed holder for a secondary receptor can be fitted, and the height of the holder adapted for taking photographs of a seated patient. When applying this holder, the aforesaid control means receives corresponding information and, optionally subsequent to the aforesaid activation of an auxiliary operating device, the beam source is automatically adjusted to its basic setting in relation to the applied secondary receptor.

Movement of the tower structure and the beam source carried thereby in the X, Y and Z directions is preferably effected with the aid of electric motors. The rotary movements carried out by the beam source are also preferably effected with the aid of an electric motor connected to the rotational axle of said source.

Manually effected setting movements of the receptor unit are transferred to the different motors for executing movement of the beam source, in a suitable known manner. In order to achieve the exactitude desired, there are preferably used analogue or digital position sensors, e.g. multi-coil potentiometers or pulse emitters suitable for the purpose in question. The system may also include means for automatic movement of the receptor unit to given preprogrammed positions.

As before mentioned, the respective components are moved to their basic settings automatically. Movement of said respective components from their basic settings is preferably effected with the aid of suitable buttons placed on a comfortably positioned operating panel, and indicating in a suitable manner, preferably digitally, deviations from said respective basic setting positions.

The invention also relates to a system of apparatus for taking X-ray photographs or the like, said system being substantially characterized by the features set forth in the accompanying claim.

Further characteristic features of the inventive method and system will be apparent from the following description of a number of exemplifying embodiments of the invention, made with reference to the accompanying drawings.

BRIEF DESCRIPTION OF THE DRAWINGS

FIG. 2 is a corresponding view in perspective, showing the beam source positioned in a basic setting for vertical beam path.

FIG. 3 is a part view illustrating the beam source in position for angled beam path.

FIG. 4 illustrates the system subsequent to inserting a secondary image-receptor holder and with the beam source in its basic setting position for horizontal beam path.

FIG. 8 is a side view, partly cut away, of an arm which projects out from the tower structure and which carries a carriage for movement of the beam source.

FIG. 9 is a horizontal sectional view illustrating the arm of FIG. 8 from above.

FIG. 10 is a horizontal sectional view corresponding to FIG. 9, subsequent to movement of the carriage and outward swinging of the beam source.

FIG. 11 is a side view, partially cut away, of another part of the tower structure shown in FIG. 1, and illustrates an arrangement for displacing the arm and the tower-carried receptor holder linearly in the Z-direction.

FIG. 12 is a side view, partially cut away, of a lower part of the tower structure shown in FIG. 1, and illustrates bottom guide means and drive motor for horizontal movement of the tower structure.

FIG. 13 illustrates in perspective part of a patient support table provided with a receptor unit and two alternative secondary receptor holders capable of being mounted in the receptor unit, on either side of the table.

DESCRIPTION OF PREFERRED EMBODIMENTS

Figure 1:
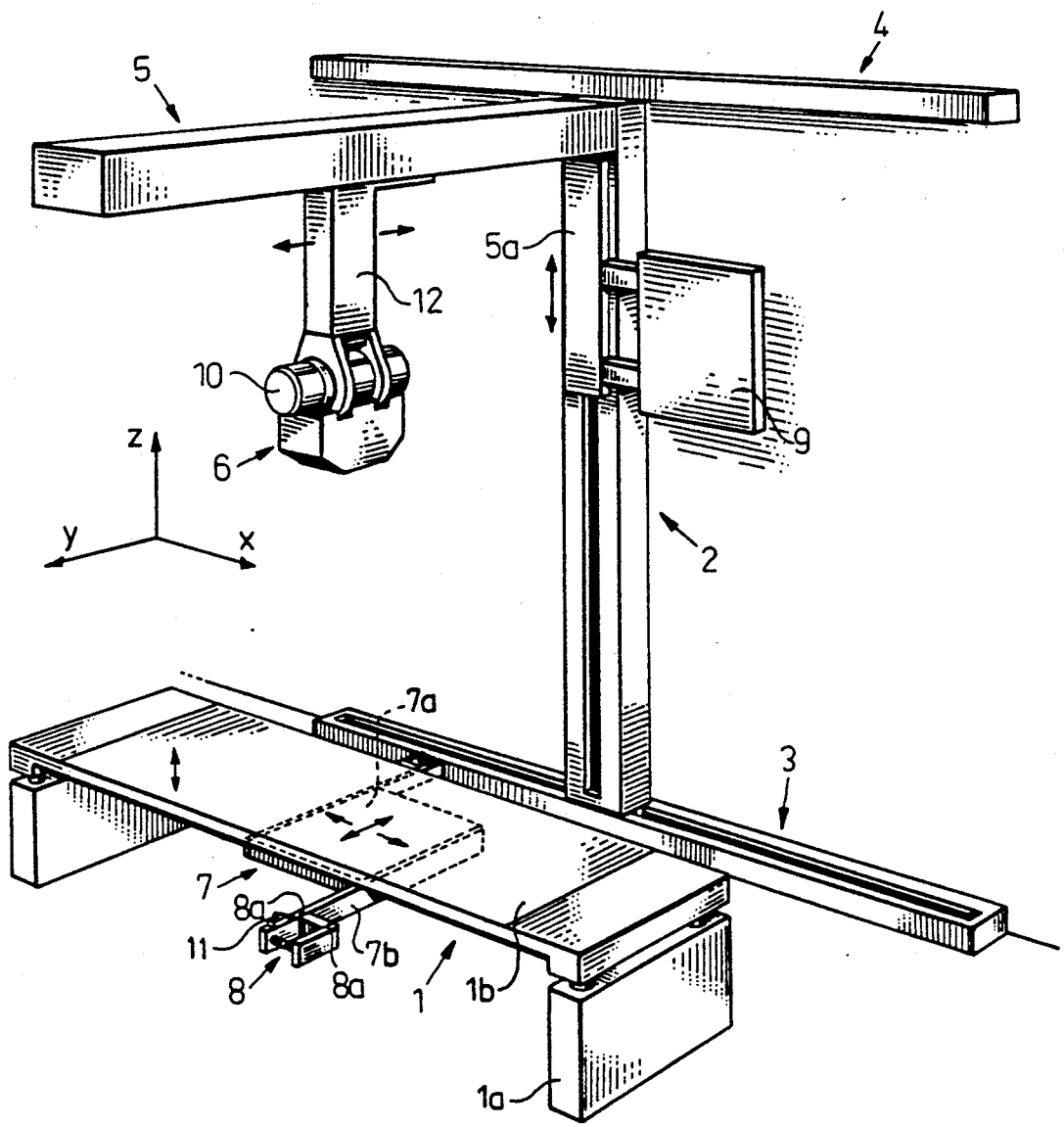
FIG. 1 illustrates in perspective a system of apparatus for X-ray photography in accordance with the invention, including a patient support table provided with an image receptor unit and a displaceable tower structure carrying a beam source.

FIG. 1 illustrates a system of apparatus for X-ray photography, comprising a raiseable and lowerable patient support table 1, which is preferably firmly mounted on the floor, and a floor-mounted and ceiling-mounted tower structure 2 carrying a beam or X-ray source. The tower structure is capable of being moved in the X-direction along the table 1 in a bottom floor-mounted guide means 3 and a top ceiling-mounted guide means 4. The tower structure 2 has projecting outwardly therefrom an arm 5 which can be moved upwards and downwards, i.e. in the X-direction.

The arm 5 carries a beam source 6 which is movable along said arm in the Y-direction and which can be swung or pivoted about a horizontal axis.

Arranged beneath the patient support table is a receptor unit or receptor holder 7 for accommodating a receptor 7a, said unit having the form of a carriage which can be moved linearly in the X- and Y-directions. Extending from each side of the unit 7 is a carrier means 7b for an operating handle 8. The unit can be caused to move in the X and Y directions by gripping the handle 8 such that the image receptor will obtain an accurately defined position in relation to the X-ray photograph to be taken. The handle 8 also incorporates a recess 8a in which an alternative secondary receptor holder 15 (see FIG. 4) for horizontal beam path can be mounted, as hereinafter described in more detail.

The outwardly projecting arm 5 carries a downwardly extending part 5a on which there is mounted a laterally projecting further holder 9 intended for receiving a tertiary or third receptor, which accompanies movement of the arm in said X and X directions.

FIG. 2 shows the apparatus of FIG. 1 adjusted to a basic setting for vertical, centered beam path onto a receptor 7a located in the receptor unit 7. The receptor may be of varying construction, size and shape and the receptor holder or "back surface" can be configured to center the receptor automatically as it is placed in the holder, irrespective of the configuration, size and shape of the receptor.

FIG. 3 illustrates the beam source 6 adjusted to a position for angled beam path, the tower structure 2 and the arm 5 having been moved in the X-direction from the position illustrated in FIG. 2 and the beam source having been rotated about a horizontal axis by a drive motor 10 through an angle α, which normally lies between 0° and 20°, depending upon the photographs to be taken. In accordance with the basic concept of the invention as disclosed above, a setting of a given angle α on an operating panel (not shown) results in movement of the tower structure 2 and the arm f through a corresponding distance, so that the beam source subsequent to rotation through said angle α about the horizontal axis emits X-rays in a manner to impinge upon a receptor located in the receptor unit 7; prior to setting the angle by means of the operating panel, the operating system as a whole is preferably deactivated by means of a separate operating device 11 (see FIG. 1) connected to or located adjacent to the operating handle 8.

In this case, displacement of the receptor unit 7 in the X and Y directions results in corresponding, programmed movement of the tower structure 2 and the outwardly projecting arm in the X-direction, and by movement of the arm 12 carrying the beam source 6 in the Y-direction.

FIG. 4 illustrates the events that take place when a secondary receptor holder 15 is mounted in holes 8a provided in the handle part 8 of the receptor unit 7. Subsequent to activating an operating device on the panel, positioning the secondary receptor holder in said holes results in downward movement of the arm 5 in the Z-direction, outward swinging of the angled arm 12, and rotation of the beam source through 90° about the horizontal axis, to a basic setting horizontal, centered beam path on a receptor located in the thus mounted receptor holder 15. Displacement of the handle in the X and Y directions, which results in corresponding displacement of both the receptor unit 7 and the receptor holder 15, also results in automatic displacement of the tower in the X-direction and displacement of the angled arm 12 in the Y-direction, along the arm 5, i.e. such that the beam source 6 is maintained in its position for horizontal, centered beam path onto the receptor in the receptor holder 15.

Figure 5:
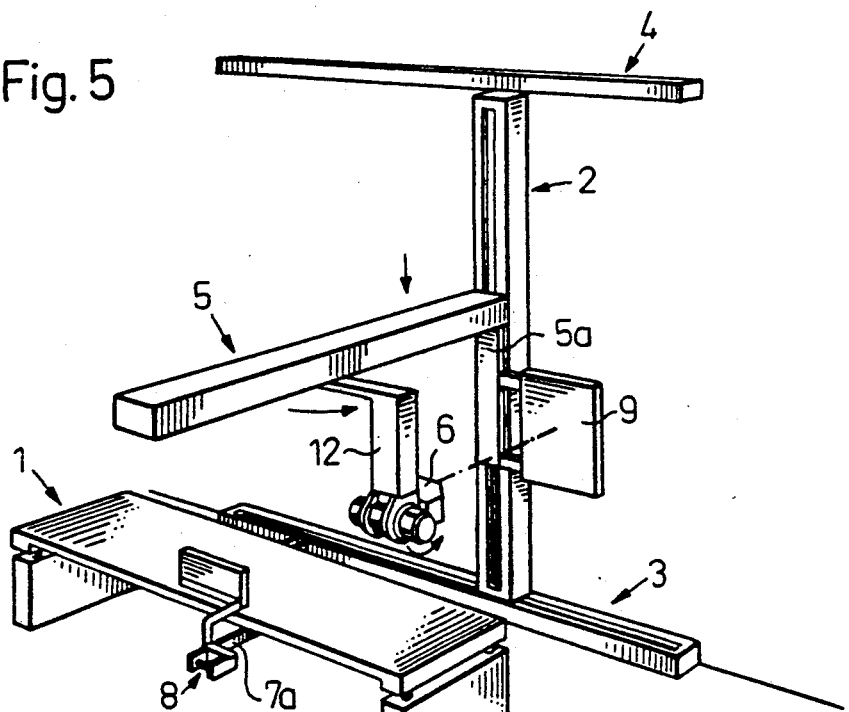
FIG. 5 illustrates the apparatus of the system set to a position for taking X-ray photographs of the lungs in particular with the aid of a tower-carried tertiary receptor holder and with the beam source positioned in a basic setting for horizontal, centered beam path on said receptor.

FIG. 5 illustrates a basic setting in which the beam source 6 is adjusted for horizontal beam path onto a receptor in tertiary receptor holder 9 carried by the arm 5 via the downwardly extending part 5a. This position is also reached automatically, upon receipt of a command signal.

This illustrated basic setting of the relevant components enables, for instance, lung photographs to be taken, with the patient located contiguous with the receptor in the holder and with his/her back facing the beam source 6. Activation of means on the operating panel for this particular basic setting results in corresponding movements of the beam source 6. It shall be observed that the receptor holder 9 and the beam source 6 carry out, in this case, mechanical synchronized movements in the X and Z directions. As will be understood, the beam source may be angled relative to the receptor unit.

Figure 7:
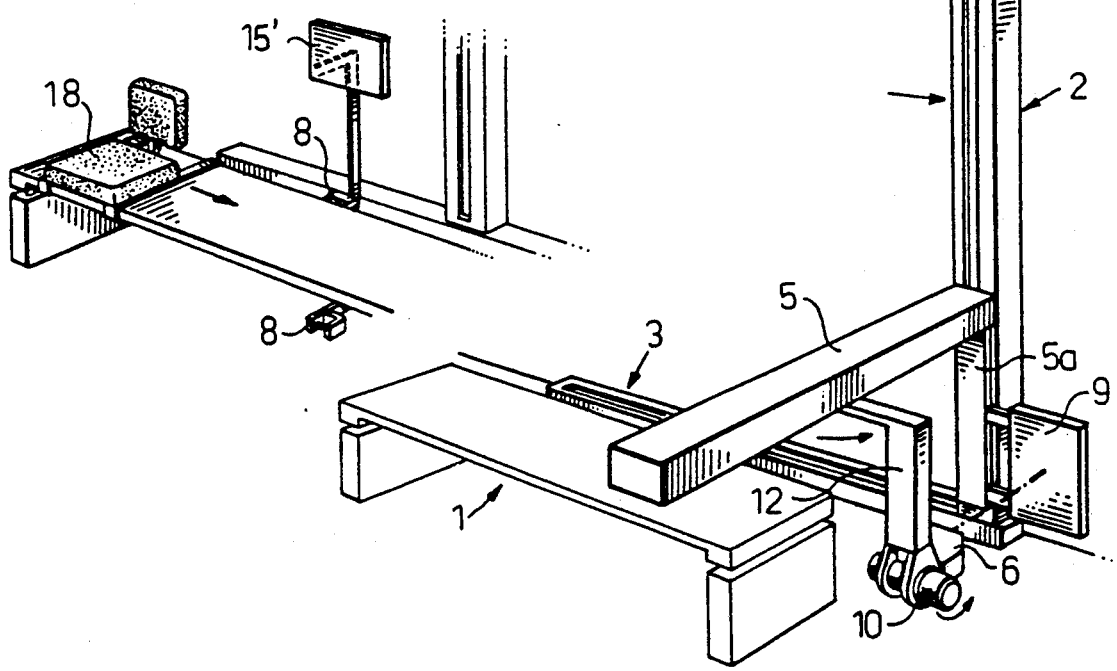
FIG. 7 illustrates the system of apparatus shown in FIG. 5 with the beam source and the receptor holder in a position for taking a photograph, e.g., of a "loaded knee" of a patient.

FIG. 7 illustrates substantially the same basic settings as those illustrated in FIG. 5, although with the difference that the receptor holder 9 and the beam source 6 have been moved downwardly in the Z-direction. This positional setting can be utilized, for instance, when taking photographs of a loaded knee, etc.

Figure 6:
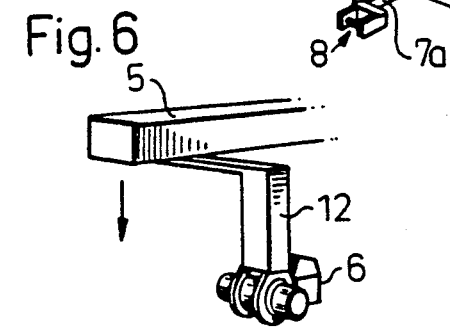
FIG. 6 illustrates one end of the patient support table which has mounted thereon a seat unit for taking X-ray photographs of a seated patient and having attached thereto a secondary receptor holder adapted for this purpose.

FIG. 6 illustrates a modification of the patient support table 1 shown in FIG. 1, the table of the FIG. 6 embodiment being lengthened so as to provide room for a seat unit 18 which enables photographs to be taken of patients in a sitting position. The illustrated seat unit 18 is movable in the width direction of the table, and is also preferably rotatable. When the seat unit 18 is used, a secondary receptor holder 15', particularly constructed to this end, is fitted in to the holes 8a (See FIG. 1) of one of the handle parts 8. The receptor holder 15' has a longer holder part than the holder 15 illustrated in FIG. 4. Application of the receptor holder 15' results in corresponding information to the operating system of the beam source, which in accordance with the aforegoing automatically adjusts the beam source to a basic setting for horizontal, centered beam path onto a receptor located in the holder 15, subsequent to activation of an operating device. The beam source can thereafter be moved from this basic setting to any of a number of desired settings.

FIGS. 8–10 illustrate an exemplifying embodiment of a drive arrangement for movement of the beam source 6 in relation to the arm 5.

The beam source 6 is carried by the angled arm 12, which is suspended from a peg 20 in a carriage 21, which is mounted on the outwardly projecting arm 5 of the tower structure and runs on ball bearings 22 in said arm. The carriage is driven by a motor 23 comprising a line pulley 23a, having extending therearound a line 24 connected to the carriage. The peg 20 carries a toothed wheel 25 on the upper side of the carriage 21. When the toothed wheel 25 passes a toothed segment 26 fixedly mounted on the arm 5, as the carriage 21 moves, the peg 20 is caused to rotate and therewith swing the beam source 6 to the position illustrated in FIGS. 4–7.

FIGS. 11 and 12 illustrate an exemplary embodiment of a drive arrangement for effecting movement of the outwardly projecting arm 5 in the Z-direction and for effecting movements of the tower structure in the X-direction.

The tower structure 2 carries a bracket structure which extends downwardly into the guide 3 and which comprises two mutually parallel parts 30, 31, of which the part 31 supports a drive motor 32. The output shaft of the drive motor supports between the bracket parts 30, 31 a wheel 33 of V-shaped profile, which runs on a guide 34 of circular cross-sectional shape. A ball bearing 34 is journalled in the lower part of the tower 2 for movement on the upper side of the guide 3. Rotation of the motor 32 results in linear displacement of the tower structure in the X-direction.

Also arranged at the bottom of the tower structure 2 is a drive motor 35 which co-acts with a screw 38 having a trapezoidal screw thread, via a gear arrangement 36, 37. The arm 5 and the downwardly projecting arm part 5a carrying the receptor holder 9 accommodate two journal parts 5b which embrace the screw 38 and exhibit corresponding trapezoidal thread sections. When the screw 38 is turned in either direction, the arm 5 and the receptor holder 9 are displaced correspondingly in the Z-direction.

FIG. 13 illustrates the aforesaid handle parts 8 located on mutually opposite sides of the table 1 and connect to the receptor unit 7 located beneath the table. The Figure also illustrates the capability of the handle parts to accomodate receptor holders 15 and 15' respectively which are intended for a horizontal beam path and which are of mutually different configuration. The connecting holes 8a in respective handle parts 8 are configured so that solely a given receptor holder can be fitted into corresponding pairs of holes. In this way, the drive system of the X-ray apparatus will receive information relating to the type of receptor holder mounted in the handle at that time, whereupon the beam source is adjusted to a corresponding setting.

Consequently, it lies within the concept of the invention to utilize a plurality of different types of secondary receptor holders which can be mounted or applied alternatively. When such a secondary receptor holder is applied, the beam source will automatically carry out corresponding movements, subsequent to activation of an operating device, such as to adopt a basic setting position for horizontal centered beam path onto the receptor in the holder in question. The holder of the FIG. 13 embodiment has a bracket part 15b provided with connecting pins 15c.

A pack of microswitches for enabling the movement combinations required for the correct function of the system may be connected to the system operating panel.

As will be seen from FIG. 13, the operating device of the illustrated embodiment has the form of a "slave button" 11 which serves as a main switch for activating and deactivating the aforesaid operational movements. This operating device, however, may alternatively have the form of a "dead mans grip" which enables the receptor unit 7 to be displaced when the handle part 8a is gripped. As will be understood, when setting the receptor unit in position, the handle is gripped and the setting movements required to move the beam source to its correct position are carried out automatically.

In the case of the inventive system, respective receptor holders, 7, 9, 15 are able to accommodate different types of receptor. For example, the receptor holder may have the form of a box, into which a cassette is inserted. The box may include an additional slot, into which a grid is inserted. Thus, when taking side photographs, it is possible to select a cassette which incorporates a grid, or a standard cassette with separate grids.

An inventive system can also accommodate all the various kinds of image receptor that can be used. In this regard, the actual receptor holder may, in certain instances, have the form of a frame into which cassettes of various sizes can be inserted, optionally with built-in grids for ease of exchange.

Figure 14:
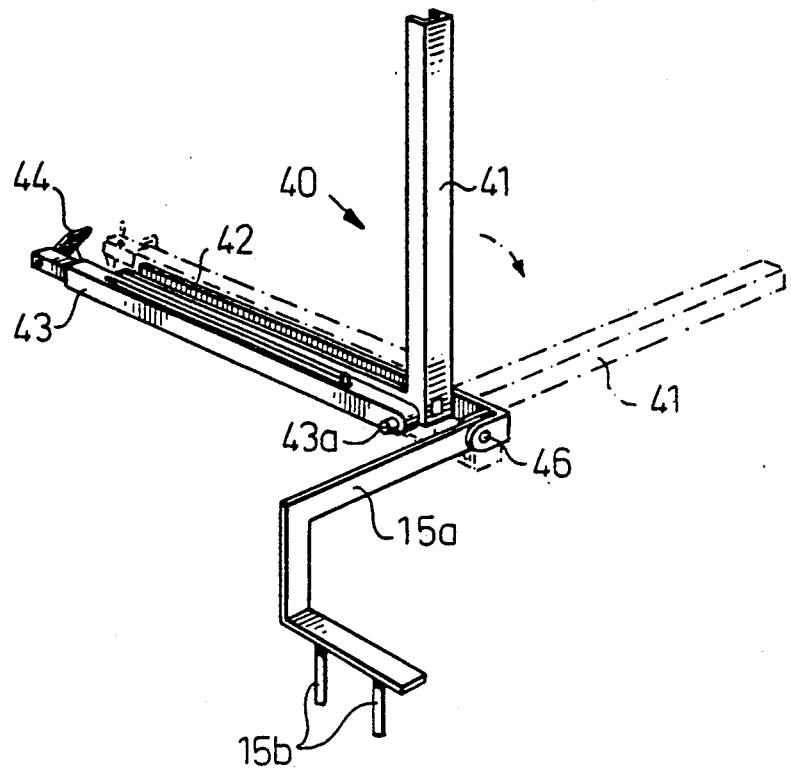
FIG. 14 is a perspective view of a universal receptor holder.
Figure 15:
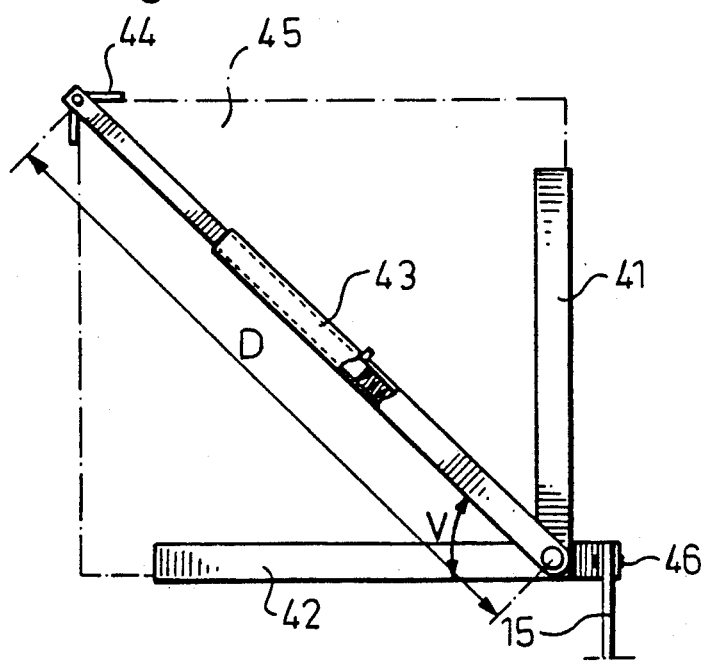
FIG. 15 is a side view of the holder shown in FIG. 14 and indicates the presence of a receptor in said holder.

An exemplifying embodiment of an alternative universal receptor holder is illustrated in FIGS. 14 and 15.

The holder 40 is intended to replace a separate holder for different image formats with a universal holder which can be used for all present day formats of, e.g., X-ray film cassettes or images plates.

The illustrated holder comprises two mutually angled rails 41, 42 which are of U-shaped cross-section and which are joined together and to an angled bracket part 15a carrying connecting pins 15b.

Journalled in the corner defined by the two mutually angled rails is a telescopic, diagonal arm 43 which can be pivoted about a horizontal axis 43a. The arm 43 carries at its outer end an angle piece 44 which engages against a receptor 45 inserted in the holder, said arm being either sprung and/or provided with manual locking means.

Although not shown, the arm 43 incorporates a sensor, e.g. a potentiometer or pulse emitter, which senses the prevailing length D of the arm.

Also arranged at the end of the arm is a further sensor (not shown) which senses the angle $v$ defined by the arm with the horizontal. Knowledge of the arm length and the angle $v$ is sufficient for determining the format of a four-cornered receptor inserted in the holder. The height of the receptor is therewith the arm length x sine v and the side of the cassette will have a length equal to the arm length x cosine v.

This facility for measuring the format of the receptor, necessary for obtaining automatic collimation, can also be used for image centering purposes, by guiding the beam source 6 for movement in the X and Z directions with the aid of an appropriate servomechanism.

The angle pieces 41, 42, 44 are provided with two or more electric switches (not shown) e.g. microswitches, which are activated by a correctly positioned image receptor 45.

These switches are connected in series with an exposure switch (not shown) which is effective in blocking an exposure if the image is incorrectly centered. This will avoid subjecting the patient to unnecessary radiation dosages.

The bracket part 15a also includes a further pivot axle 46 which enables the universal holder 40 to be pivoted to a horizontal position, shown in broken lines in FIG. 14. Further electric switches (not shown) indicate to the operating system whether the receptor holder has a vertical or a horizontal position and prevents exposure when the receptor holder occupies an intermediate position. In many cases of simple X-ray photography, for example photographing a hand or an arm it is sufficient for the patient to position the part of the body to be photographed on a receptor, and then to simply take a photograph. In the case of a universal holder of the kind illustrated in FIGS. 14 and 15, this procedure is facilitated when the holder can be swung to a horizontal position, in the manner indicated, so that the exposure can be made with the beam or radiation source in a vertical position.

In many instances it is desirable to subject the patient to the least possible movement, particularly if the patient is badly injured or unconscious. In this regard, the present invention provides the possibility of taking X-ray photographs of a patient positioned on, e.g., a wheeled stretcher, without needing to move the patient from the stretcher. This can be achieved by ensuring that the patient support table 1b can be removed, wherewith the receptor unit 7 (of FIG. 1) in the form of a carriage which can be displaced linearly in the X-direction and Y-direction and which is movable in its frame or stand is exposed. The movable stretcher can then be moved into position and the receptor holder moved as close as possible to the underside of the stretcher. The inventive facility of synchronizing movements of the receptor unit and the beam source is also utilized in this case.

Figure 16:
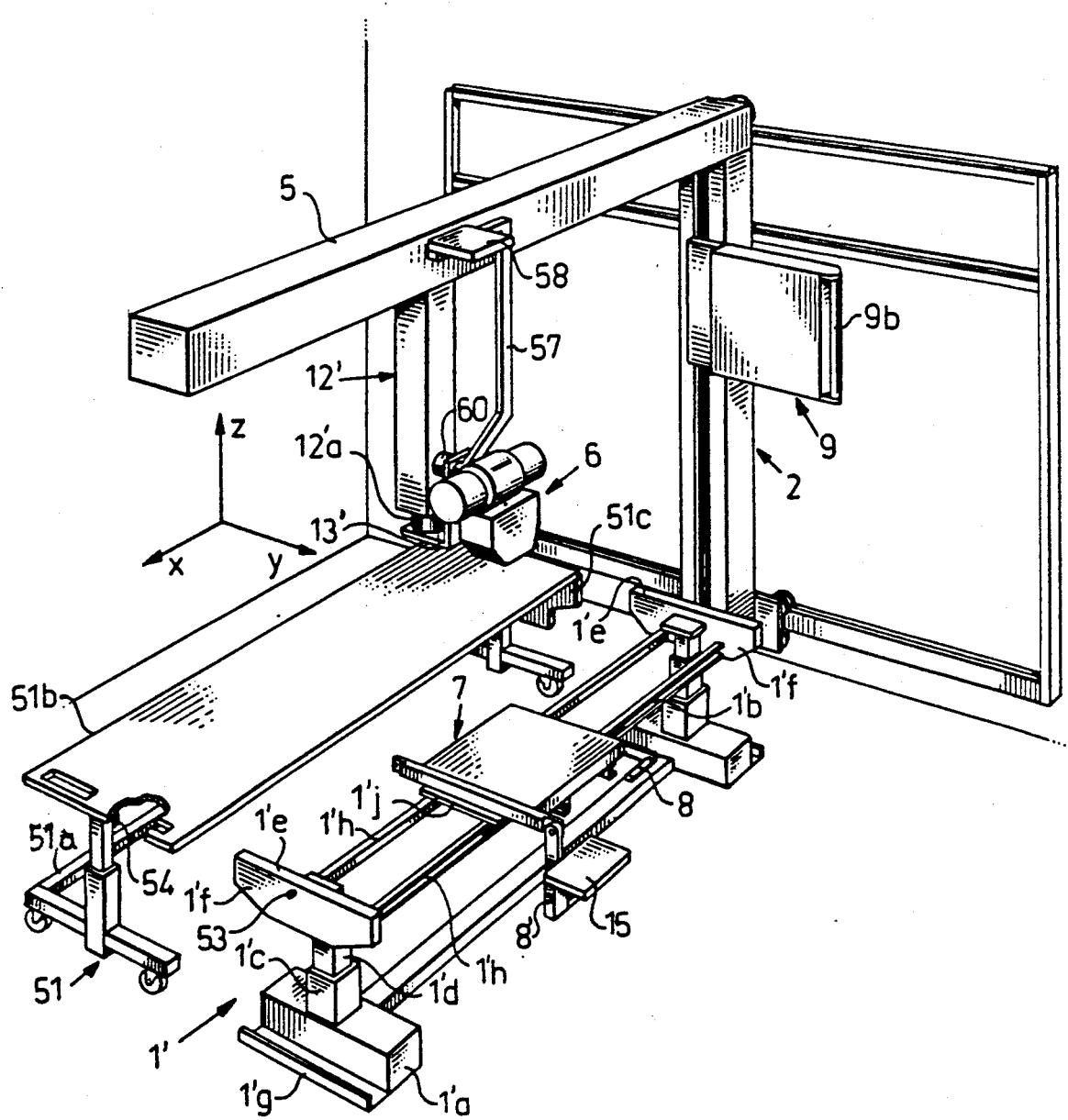
FIG. 16 is a perspective view of an alternative system of apparatus, in which the patient support table extends perpendicularly to a wall structure and the X and Y axes have subsequently changed places. This system of apparatus also includes a number of additional modifications to previously illustrated embodiments.
Figure 17:
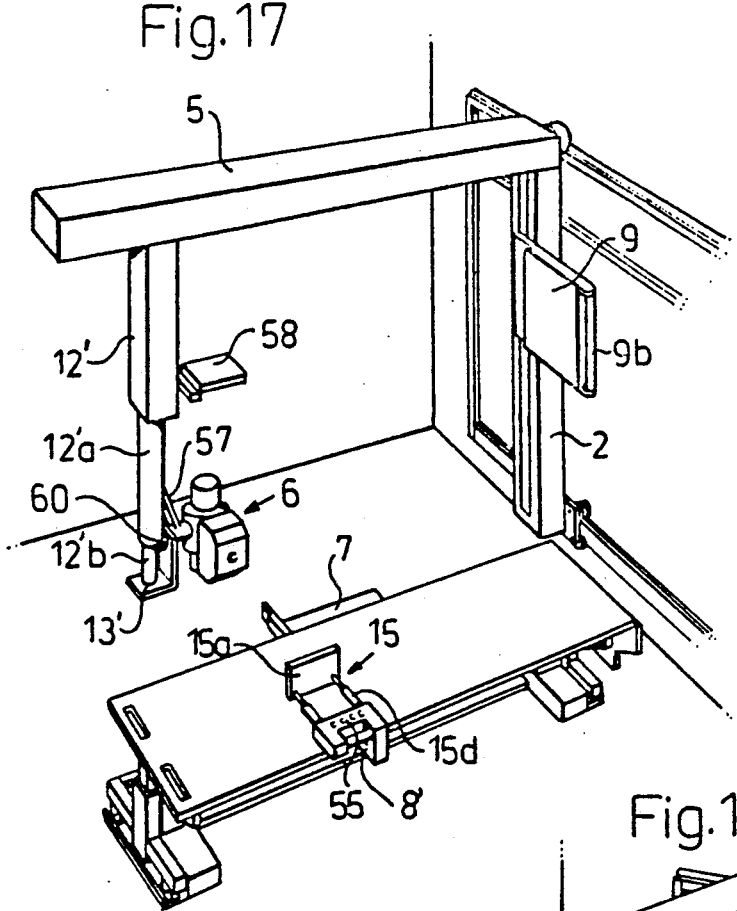
FIG. 17 illustrates in perspective a system of apparatus according to FIG. 16 in an operative state.
Figure 18:
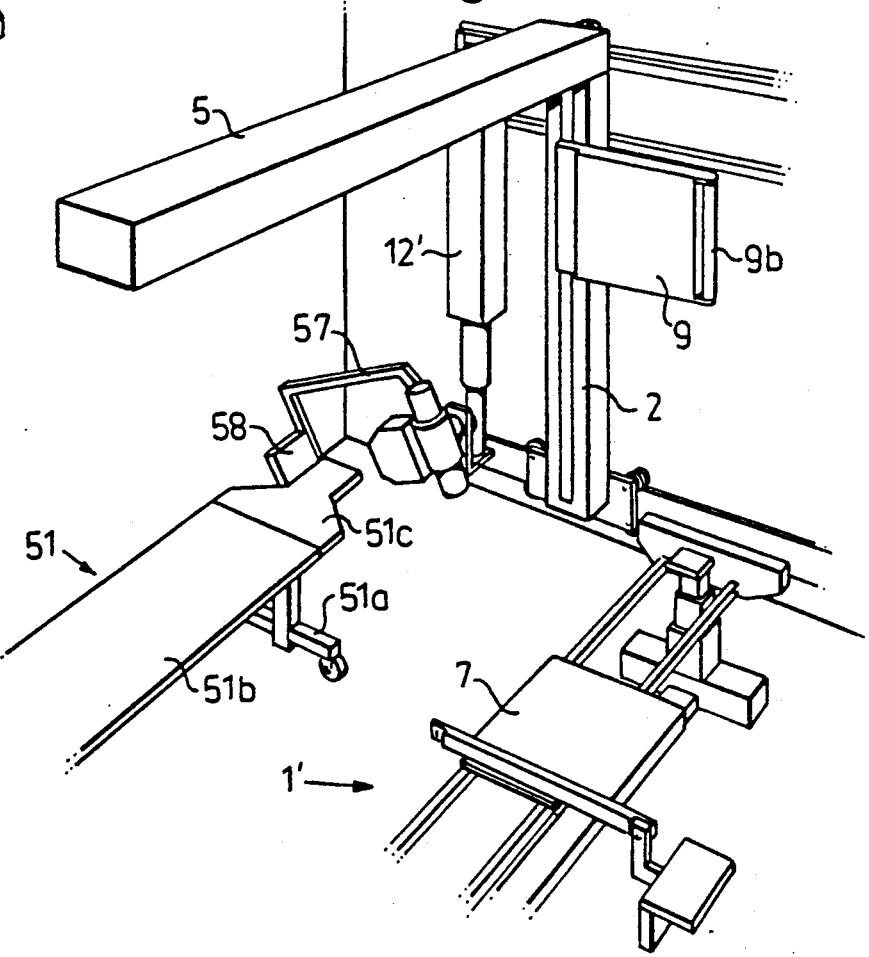
FIG. 18 illustrates further a method of use of a system according to FIG. 16 and 17.

FIGS. 16–18 illustrate the principle construction of the system of apparatus described, the illustrated system, however, being modified to some extent in relation to the aforedescribed embodiments.

It should be noted that the patient support table, the table top of which has been removed so as to leave the table stand 1', extends at right angles to the wall along which the tower structure 2 can be moved. As before mentioned, the reference to movement in the "X-direction" still implies movement which is parallel with the longitudinal axis of the table, which thus means that the X and Y axes have changed places. Consequently, when moving in the horizontal plane the tower structure 2 moves in the Y-direction in FIG. 16.

The arm 5 projecting outwardly from the tower structure 2 and carrying the beam or radiation source 6 is firmly connected to the tower 2 and is thus movable in the Y-direction together with said tower. The beam source 6 is carried by a telescopic arm 12', such that the beam source can move in the Z-direction. The arm 12' is also movable in the X-direction along the arm 5. As with the aforedescribed embodiments, the beam source can also be pivoted about a horizontal axis.

The table stand 1' is complemented by a mobile table unit 51 having a wheeled frame 51a and a table top 51b. In this case, the mobile unit 51 has the form of a wheeled stretcher.

The stand 1' comprises stand parts 1'a having a telescopic arrangement 1'c, 1'd which carries an end support 1'f on which there is provided a supported surface 1'e for supporting the table top 51b. The end support 1'f is joined with elongated guides 1'h in which the receptor unit 7 is mounted. The stand 1' also includes transverse guides 1'j for guiding movement of the receptor unit in the Y-direction. The wheels of the unit 51 are guided in floor guides 1'g.

The support surfaces 1'e arranged on the end supports 1'f and supporting the table top 51b of the mobile unit 51 are inclined so that when the mobile unit 51 is moved in above the stand 1', wherewith a guide in respective surfaces 1'f ensures that the mobile unit takes its correct position, the wheels of the unit are lifted slightly away from the floor. When the mobile unit is moved in over the stand, the unit and stand are connected together automatically, with the aid of mutually co-acting locking means 53, 54 which "click" into one another. The telescopic function of the mobile unit is disengaged when coupling the mobile unit with the stand 1', so that the table top 51b will follow movements of the stand 1' in the Z-direction, through the agency of its telescopic arrangement 1'c, 1'd.

As before mentioned, a receptor unit 7 can be moved along the stand 1', and the application of a secondary receptor holder 15 to said receptor unit results in movement of the beam source 6 in the Z-direction and displacement of the tower stand and the beam source in the Y-direction and optionally the X-direction, together with rotation of the beam source about its horizontal axis to a basic setting for a horizontal ray path, as with the FIG. 1 embodiment.

The secondary receptor holder 15 of this embodiment includes a pivoted arm 8', which enables the receptor holder 15 to be dropped to a parking position. As illustrated in FIG. 17, the receptor holder 15 can be swung up to an active position, in which the receptor holder is applied. Additionally hereto, an operating device on a panel 55 is activated for activation of the receptor.

In the case of the FIG. 17 embodiment, the secondary receptor holder 15 is provided with telescopic arms 15d. This enables movement in the Y-direction to be utilized from the edge of the table to its center line. Application of the receptor holder from the other direction enables the whole of the patient area on the table top to be covered from two directions.

It will be seen from this that the embodiment illustrated in FIGS. 16–18 have a number of additional characteristic features. Thus, although the embodiment according to FIGS. 16–18 has a tertiary receptor holder 9 similar to the embodiment of FIG. 1, the receptor holder of the FIGS. 16–18 embodiment is not connected to the arm 5. Instead, the receptor holder 9 is carried in the frame 2 and balanced by a counterweight (not shown). When the receptor holder 9 is activated, e.g. from the operation panel 55, the beam source 6 will move to a basic setting for horizontal beam path at a predetermined SID.

Activation of the receptor holder 9 through a handle 9b will result in corresponding automatic movement of the telescopic arrangement 12' with the parts 12'a, 12'b, so that the beam source 6 will always take an accurately centered position.

As will be seen from FIG. 16, the beam source 6 is also joined to one end of an approximately Z-shaped arm 57 which carries a fourth receptor holder 58 at its other end. The arm 57 is pivotal about the same geometric axis as the beam source 6 and can be set to various rotational positions.

FIG. 18 illustrates an application in which the stretcher carriage 51 has an upwardly pivotable end part 51c. The Figure illustrates how an X-ray photograph can be taken, for instance, of the skull of a patient with the aid of the fourth receptor holder 58, when the stretcher carriage is in a free position, i.e. not connected to the stand 1'. This enables the best exposure angle to be chosen in relation to the patient (not shown). With regard to the alternative embodiment illustrated in FIGS. 16–18, the beam source 6 may be swung about its horizontal axis with the aid of a setting motor (cf FIG. 17) arranged on the angled shelf 13' connected to the lower part 12'b of the telescopic arm 12', and can be swung about a vertical axis with the aid of a further motor (not visible in FIG. 17). When the mobile unit 51 is disengaged from the stand 1', the telescopic arrangement on the tower structure will be activated such that the table top 51b will remain at the set height. The possibility of changing the height of the stand 1' is blocked at the same time.

An alternative embodiment is also conceivable in which the table top 51b is left on the stand 1' and the actual wheeled frame is removed, for instance to provide the stand with another table top 51.

Figure 19:
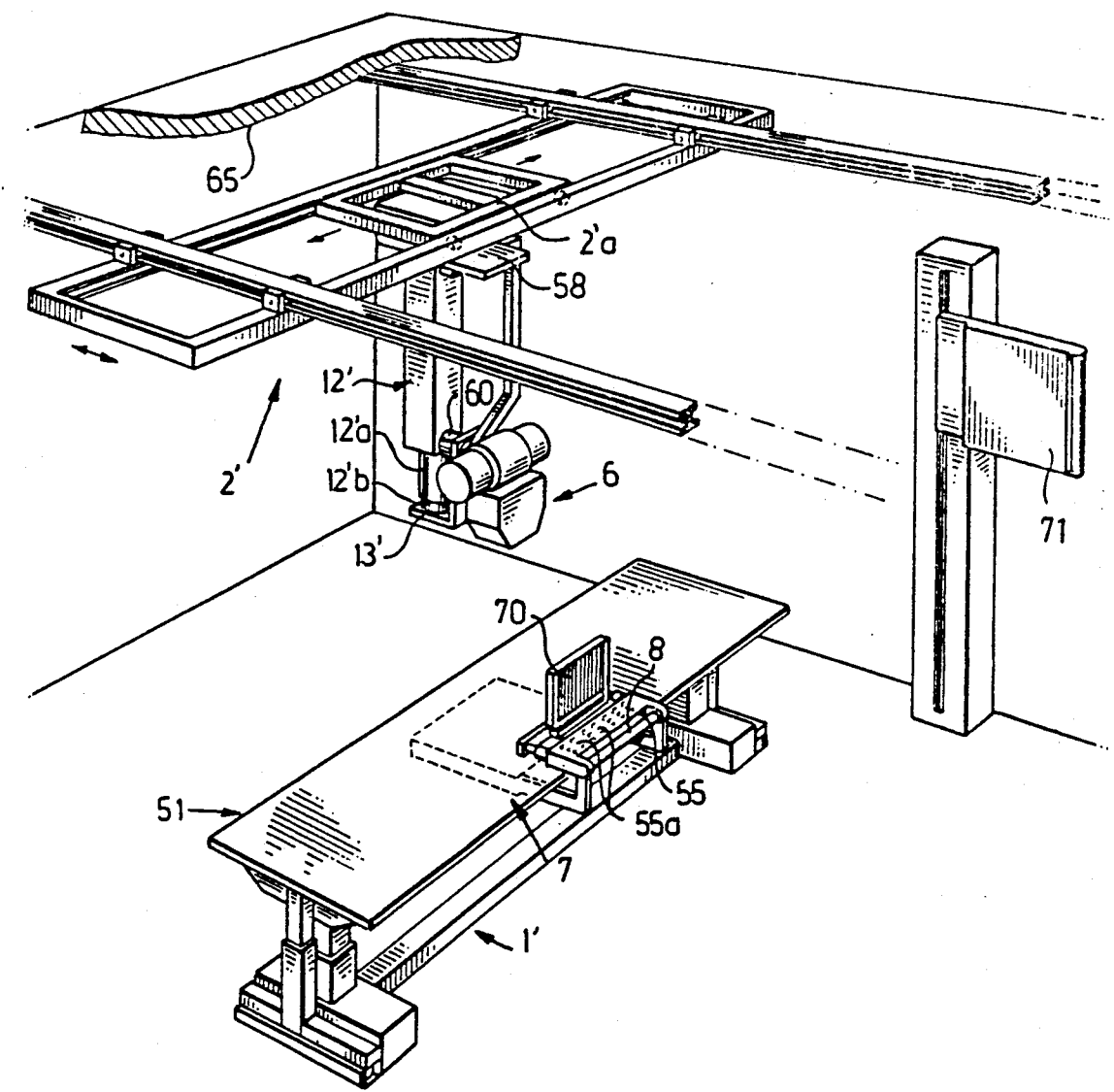
FIG. 19 is a perspective view which illustrates a further embodiment in the form of a ceiling-mounted tower or column structure and a receptor unit provided with a fixed secondary receptor holder.

FIG. 19 illustrates a further embodiment in which the beam source 6 is carried by a ceiling-mounted frame structure 2' via a telescopic arm arrangement 12'. The ceiling is referenced 65 and a carriage associated with the frame 2' and capable of moving in the X-direction and Y-direction is referenced 2'a. The carriage supports the telescopic arm arrangement 12', said telescopic arm including parts 12'a and 12'b. The beam source 6 can be mounted on the part 12'b of said telescopic arm by means of an arrangement corresponding to that illustrated in FIGS. 16–18. The beam source can be swung about a horizontal axis with the aid of a motor 60. In the case of this embodiment, the receptor unit 7 carried by the table 1 has the form of a stationarily mounted holder 70 for a secondary receptor. In this case, the arrangement is such that the fixed arrangement of the secondary image receptor will not have any substantial deleterious influence on the use of the receptor unit for taking photographs with a vertical beam or ray path and will not unnecessarily impede the work of the operator in, for instance, carrying out adjustments.

The beam source 6 also co-acts with a tertiary receptor holder 71 fixedly arranged in the X-direction and Y-direction. The holder 71 is preferably located adjacent a wall in the room in which the X-ray system is located, in a manner so as not to obstruct as far as possible the remaining activity carried out in the room.

The holder 71 can only be moved in the vertical direction and is primarily intended for taking lung X-ray photographs, although it can also be used for other purposes.

In the case of this embodiment, the operating panel 55 of the receptor unit 7 has approximately the same length as the actual unit (i.e. extension in the X-direction).

The operating panel 55 includes a plurality of press buttons 55a which are provided with signs indicating the various positions of the beam source 6. The operating panel also includes buttons for activating the various receptors present and therewith enabling positional adjustments to be made to the beam source.

The operating panel also conveniently includes separate buttons for zero-setting at selected receptor unit positions, so that different desired and also registrable settings of the receptor unit from such a zero-setting can be undertaken with corresponding movement of the beam source subsequent to activating the beam source drive means.

This embodiment also suitably includes a so-called touch-handle 8 located in the proximity of the operating panel 55 for setting movements of the receptor unit.

Figure 20:
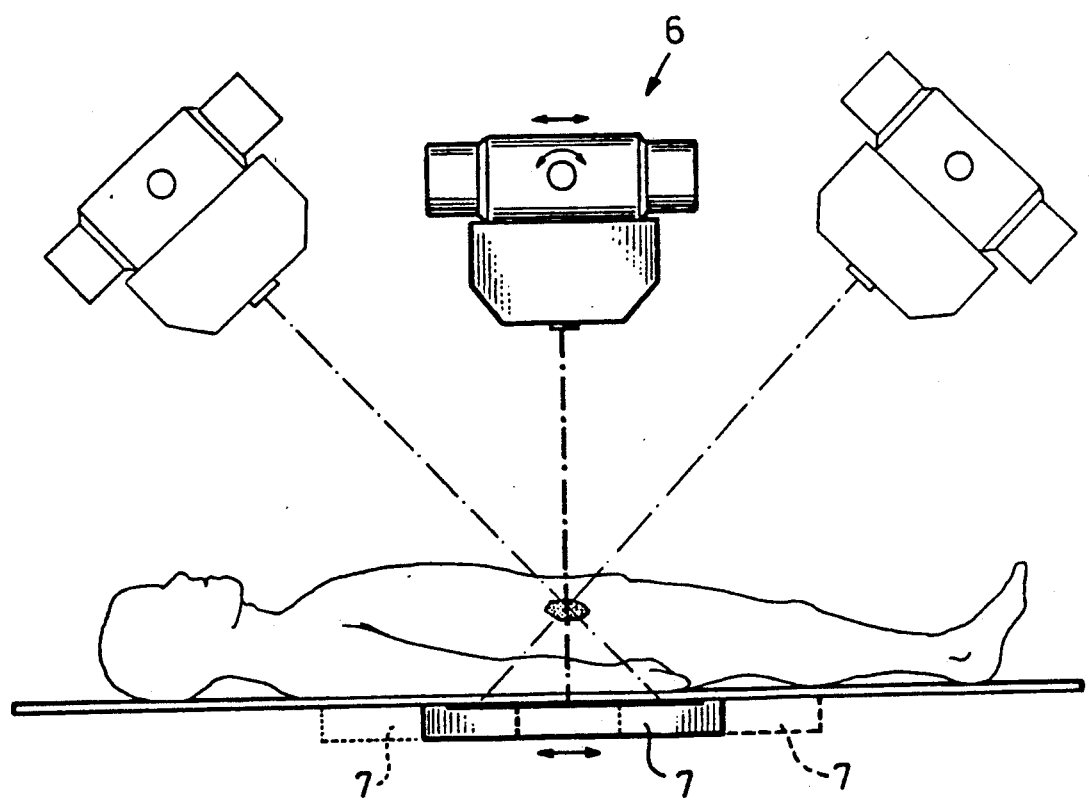
FIG. 20, finally, illustrates the principle of use of a system of apparatus according to the invention for linear tomography.

FIG. 20 illustrates the improved possibilities afforded by an inventive system when carrying out X-ray tomography. The layer height can be changed by varying the distance travelled by the receptor relative to focus.

An inventive system is able to engender two mutually unconstrained movements, viz. movement of the beam or radiation source 6 and movement of the receptor holder 7 with its receptor 6a. These movements are not mechanically coupled. Consequently, no separate function is required for changing the layer height, since this possibility is found incorporated in the system. The system thus enables simple variation of the layer height.

Furthermore, the system enables the film speed to be varied during the actual exposure, for the purpose of obtaining angled layers. In this case, a progressive increase in speed will provide the same effect as an increase in layer height during an exposure.

A conventional image amplifier (not shown) for irradiation of the patient can also be mounted on the inventive receptor unit.

The type of grid used together with a receptor in a given case can be entered into the operating panel, wherewith the system will detect the collimation undertaken. The values inserted into the operating panel may suitably be shown on a display device. A given type of grid, or raste, has a pre-determined number of lines/centimeter and "ratio", i.e. the ratio of grid height/lamella spacing. When inserting the line number and "ratio" tabled values of SID-tolerance are found available for each grid, e.g. in softwear form. The SID-tolerance may also be changed for increased collimation. It is possible in this way to ensure that the grid concerned will be located within the SID-range permitted by the grid.

In summary, the exposure can be controlled automatically and the highest degree of collimation possible can be achieved. Furthermore, it is possible to deviate from the focus-distance concerned in different individual cases, which contributes to optimum image quality, which, in turn, forms a basis for a correct diagnosis and reduces the risk of the patient being subject to unnecessary radiation dosages.

It is also possible to replace an X-ray cassette with some other form of radiation receptor. For example, it is possible to use image plates, which normally have the same external measurements as X-ray film cassettes and the ability of which to absorb radiation corresponding to an X-ray image is used for electronic image storage.

INDUSTRIAL APPLICATION

As will be understood from the aforegoing, the invention provides the important advantage of enabling the operator to work at a comfortable height and ensures that the operator need only handle a small mass when adjusting the settings of the receptor unit in the X-direction and Y-direction. The work carried out by the operator can be facilitated still further by utilizing the movements performed by the holder when changing a receptor to automatically decenter and center the receptor in both the x-direction and the Y-direction, the decentering movement releasing the receptor for replacement with another receptor.

The possibility of removing the patient support table and moving a wheeled stretcher over the receptor unit, which is located in an underlying frame element, is another particularly important advantage afforded by the invention. This obviates the need to manipulate a seriously injured patient. The aforedescribed simple receptor-unit adjustment possibilities remain and the beam or radiation source is positioned automatically subsequent to placing the primary receptor holder on the receptor unit located beneath the table, or subsequent to placing a secondary receptor holder on said unit. All X-ray equipment know hitherto assumes that the patient needs to be manipulated, at least when photographing certain parts of the body or body organs. The basic concept of the invention obviated substantially all such need to manipulate or re-arrange the patient.

The advantages afforded by the invention are contingent on receptor and beam-source co-action incorporated in the system. The operator decides in each individual case which receptor shall be used, and takes the necessary steps for applying or activating this receptor, e.g. by pressing corresponding buttons on the operating panel, whereafter the beam source is moved automatically to a basic setting position corresponding thereto. A desired receptor can be applied or fitted, e.g., by swinging the receptor from a lowered position (parking position) on one side of the table top, or beneath the table top.

It is possible by pressing a separate button on the operating panel, e.g. in the case of an emergency, to cause the equipment applied to move rapidly and effectively to an unimpeding position, to a parking position, so that the necessary measures can be taken immediately without obstruction by the X-ray equipment and without the patient being injured in any way.

I claim:

1. A method of X-ray photography in which there is used a beam or radiation source which is carried for movement in the X, Y and Z directions and can be rotated about a horizontal axis, a patient support table and a receptor unit which is carried beneath the table for movement in the X- and the Y-directions and which when displaced linearly results in automatic movement of said source, characterized in that activation of a secondary receptor associated with the receptor unit and extending in the vertical plane results in automatic movement of said source to a basic setting for a horizontal, centered beam path on the secondary receptor.

2. A method according to claim 1, characterized in that activation of the receptor unit located beneath the patient support table causes said source to return to a basic setting-for vertical beam path onto the receptor unit.

3. A method according to claim 1, characterized in that the secondary receptor is placed on a holder which is associated with the primary receptor unit and movable together therewith, prior to activating the secondary receptor.

4. A method according to claim 1, characterized in that adjustment of said source to a setting for an angled beam path results in corresponding displacement of one of said receptors in the X-direction and/or the Y-direction for constant source-image-distance.

5. A system for X-ray photography comprising
   a) a patient support table (1; 1', 51) which includes a receptor unit (7; 40) arranged for horizontal movement beneath the table;
   b) a beam or radiation source (6) which is arranged for movement in the X, Y and Z direction and capable of being rotated about a horizontal axis; and
   c) drive means for effecting linear displacement and rotational movement of said source (6), said drive means causing movement of said source subsequent to movement of the receptor unit (7; 40), characterized in that
   d) the receptor unit (7) is configured to also accomodate a holder (15, 15'; 40; 70) intended for receiving a vertically extending secondary receptor for a horizontal beam path, and
   e) the system includes operating means so constructed that activation of the secondary receptor will cause an impulse to be sent to the drive means so that said source (6) is adjusted to a basic setting for horizontal centered beam path onto the secondary receptor.

6. A system according to claim 5, characterized in that the receptor unit (7) is configured to receive different kinds of secondary receptor holders (15; 15'; 15''; 40; 70).

7. A system according to claim 6, characterized in that said source (6) is carried by a frame structure (5) which also carries a tertiary receptor holder (9); and in that said source (6) is intended to take a third basic position relative to said tertiary receptor holder subsequent to activation of an operating device.

8. A system according to claim 7, characterized in that one end of the patient support table has arranged thereon a seat unit (18), which can be moved in the Y-direction, and a secondary receptor (15') corresponding to said seat unit and capable of being placed in said receptor unit.

9. A system according to claim 5, characterized in that the patent support table comprises a stand (1'), which carries the receptor (7), and a mobile unit (51) which comprises a table top (51b) and which can be moved in over the stand (1'), said mobile unit being detachably connectable to the stand and subsequent to being coupled thereto accompanies the setting movements of the stand in the Z-direction.

10. A system according to claim 9, characterized in that the system includes a frame structure and said source (6) is carried by a telescopic arrangement (12') connected to the frame structure (2,5; 2') of the system.

11. A system according to claim 10, characterized in that the receptor unit (7) is provided adjacent holder means (8: 8a; 8') for the secondary receptor with an operating panel (55) provided with means for activating the drive means.

12. A system according to claim 11, characterized in that the secondary receptor holder (40) comprises two rails (41,42) of U-shaped cross-section which forms a corner angle of 90° with one another, and a telescopic arm (43) which is pivotable about an axle located in said corner, said telescopic arm having provided at one end thereof engagement means (44) for engagement with a receptor (45) placed in the holder, the prevailing length of the arm and the prevailing angle defined by said arm with the horizontal providing a measurement for the dimensions of the cassette inserted in the holder.

13. A system according to claim 12, characterized in that the holder (40) is arranged on a bracket structure (15a) provided with connecting pins (15b) and capable of being pivoted about an axle (46) to a horizontal position.

14. A system according to claim 9, characterized in that the top (1b) of the patient support table (1) can be removed to permit a mobile unit, (51) to be moved in over the stand (1') fitted with the receptor holder (7).

15. A system according to claim 14, characterized in that said source (6) can be rotated about a vertical axis and is activated for such rotary movement by a motor.

* * * * *